(12) United States Patent
Kuznetsov (10) Patent No.: US 7,855,296 B1
(45) Date of Patent: Dec. 21, 2010

(54) METHOD FOR SYNTHESIZING 2-CARBOMETHOXYTROPINONE

(75) Inventor: Vladimir F. Kuznetsov, Cody, WY (US)

(73) Assignee: Cody Laboratories, Inc., Cody, WY (US)

( * ) Notice: Subject to any disclaimer, the term of this patent is extended or adjusted under 35 U.S.C. 154(b) by 577 days.

(21) Appl. No.: 11/303,309

(22) Filed: Dec. 16, 2005

(51) Int. Cl.
*C07D 451/00* (2006.01)
(52) U.S. Cl. ..................... 546/127; 546/132
(58) Field of Classification Search ............ 546/132, 546/127
See application file for complete search history.

(56) References Cited

FOREIGN PATENT DOCUMENTS

GB 214917 A * 5/1924

OTHER PUBLICATIONS

Lee et al., Journal of Organic Chemistry, 2000, vol. 65, 4773-475.*
Casale J.F. *A Practical Total Synthesis of Cocaine's Enantiomers.* Forensic Science International 33, 275-298 (1987) HTML by Rhodium—www.rhodium.ws. Chemistry Archive.
Findlay S.P. *Concerning 2-Carbomethoxytropinone.* 2-Carbomethoxytropinone, Nov. 1957, 1385-1394.
Lin R. et al. *Enantiospecific Synthesis of Natural (−)-Cocaine and Unnatural (+)-Cocaine from D- and L-Glutamic Acid.* J. Org. Chem 1998, 63, 4069-4078.
Mans D.M. et al. *Total Synthesis of (+)-Cocaine via Desymmetrization of a meso-Dialdehyde.* Organic Letters, vol. 6, No. 19, 2004, 3305-3308.

* cited by examiner

*Primary Examiner*—D. Margaret Seaman
*Assistant Examiner*—Niloofar Rahmani
(74) *Attorney, Agent, or Firm*—Merchant & Gould (57) ABSTRACT

Disclosed is a method of making (−)-cocaine efficient for use on a large scale. The cocaine is created by reacting an aqueous solution of (+)-2-carbomethoxytropinone (2-CMT) bitartrate, sodium amalgam and an acid that forms a highly soluble sodium salt to form (−)-methylecgonine. (−)-Methylecgonine is converted into (−)-cocaine. Sodium amalgam is continuously supplied from an electrolyzing unit to a reactor containing the aqueous solution of (+)-2-carbomethoxytropinone bitartrate and spent amalgam is continuously removed and regenerated. The aqueous solution is prepared by adding (rac)-2-CMT in chloroform to a solution of (+)-tartaric acid in water to create an aqueous phase having diastereomeric salts of 2-CMT with (+)-tartaric acid. An organic solvent is added to the aqueous phase and the crystals obtained from the combined aqueous phase and organic solvent are dried to obtain substantially pure crystalline (+)-2-carbomethoxytropinone bitartrate. The (rac)-2-CMT in chloroform is prepared by extracting 2-CMT from a citric acid solution.

24 Claims, 5 Drawing Sheets

Mannich type condensation of succinedialdehyde, methylamine and acetonedicarboxylic acid methyl ester

METHOD FOR SYNTHESIZING 2-CARBOMETHOXYTROPINONE

BACKGROUND OF THE INVENTION

Cocaine is a useful therapeutic used in many different products such as nasal spray. The first total synthesis of cocaine was published in 1923 by Wilstätter, Wolfes and Mader. The procedure was modified and significantly improved in the works of Findlay and then Casale. It involved preparation of racemic 2-carbomethoxytropinone, resolution of the racemate and reduction of the resulting enantiomerically pure 2-carbomethoxytropinone by sodium amalgam to obtain methyl ecgonine. Benzoylation of the latter afforded cocaine. To the best of our knowledge this is still the most convenient and practical procedure reported in the literature. However, this synthesis remains laborious, time consuming, requires distillation of large quantities of organic solvents and involves tedious separation of enantiomers.

Novel synthetic approaches to enantiomerically pure cocaine although elegant, can hardly be used for a large scale production as they involve complicated multistep synthesis and use rather expensive chemicals.

SUMMARY OF THE INVENTION

Various embodiments of the present invention relate to a method for the cost-effective, large scale synthesis of (−)-cocaine. The method has the following advantages making it suited to the large scale production of cocaine:

- The reaction mixture for the preparation of 2-carbomethoxytropinone is approximately 8 times more concentrated.
- Application of "double extraction" greatly reduces the volume of chloroform required for extractions and completely eliminates the need for distillation of the solvent.
- Isolation and purification of racemic product is not required, enantiomerically pure (+)-2-carbomethoxytropinone bitartrate is isolated directly from the reaction mixture and used in the next step "as is" without converting to a free base.
- The reaction mixture for the preparation of methyl ecgonine is approximately four times more concentrated due to application of formic acid instead of sulfuric acid.
- Sodium amalgam is constantly made by electrolysis and pumped to a reactor where it reacts with 2-carbomethoxytropinone. Spent amalgam depleted of sodium flows back to the electrolyzing unit where it is replenished with sodium. The process continues until substantially all 2-carbomethoxytropinone is converted. Thus two separate steps: preparation of sodium amalgam and reduction of 2-carbomethoxytropinone are combined into a single uninterrupted process.

In one aspect, the present invention is a method of manufacturing (−)-cocaine by reacting an aqueous solution of (+)-2-carbomethoxytropinone bitartrate, sodium amalgam and an acid that forms a highly soluble sodium salt whereby at least some of the (+)-2-carbomethoxytropinone bitartrate is converted to (−)-methylecgonine. The (−)-methylecgonine is then converted into (−)-cocaine. The method is suitable for large scale manufacture of cocaine which can then be used to create derivative products such as nasal spray.

The acid that forms a highly soluble sodium salt is an acid that forms a sodium salt that is at least 1.5 times more soluble than sodium sulfate in water at a pH of 5.6 and at a temperature of 5° C. For example, the acid may be one or more acids selected from formic acid, acetic acid, propionic acid, phosphoric acid, trifluoroacetic acid, and choroacetic acid.

In the method, the sodium amalgam is continuously supplied from an electrolyzing unit to a reactor containing the aqueous solution of (+)-2-carbomethoxytropinone bitartrate and an acid that forms a highly soluble sodium salt. The spent amalgam may further be continuously removed from the reactor and transferred to the electrolyzing unit for regeneration.

In another aspect, the aqueous solution of (+)-2-carbomethoxytropinone bitartrate may be prepared by adding (rac)-2-CMT in organic solvent not miscible with water, such as chloroform, to a solution of (+)-tartaric acid in water to create an aqueous phase having diastereomeric salts of 2-CMT with (+)-tartaric acid. An organic solvent, such as methanol, ethanol, isopropanol, acetone or some combination of solvents miscible with water, is added to the aqueous phase and the crystals obtained from the combined aqueous phase and organic solvent are dried to obtain substantially pure crystalline (+)-2-carbomethoxytropinone bitartrate. The substantially pure crystalline (+)-2-carbomethoxy-tropinone bitartrate may then be dissolved in water at a pH of 2.0 or higher.

The (rac)-2-CMT solution may be prepared by extracting 2-CMT from the aqueous reaction mixture with a solvent not miscible with water preferably with chloroform. The obtained extract is then re-extracted with a small volume of aqueous solution of an acid, which forms soluble salt with 2-CMT. Citric, acetic, formic, tartaric, hydrochloric and other acids can be used for this purpose. The organic solvent after the re-extraction is used for another extraction of 2-CMT from the reaction mixture and then re-extracted again with the same aqueous solution of an acid. The extraction—re-extraction sequence is repeated until most of the 2-CMT is transferred from the reaction mixture to the acidic aqueous solution. This "double extraction" procedure allows for preparation of concentrated solution of 2-CMT in water without any distillation using relatively small amount of organic solvent as a transferring agent. The concentrated acidic solution is then basified and extracted with organic solvent, such as chloroform. Approximately 3 times less chloroform is required for exhaustive extraction of 2-CMT from this solution as compared to the amount necessary for direct extraction from the reaction mixture.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of at least one embodiment of the invention.

In the drawings.

DETAILED DESCRIPTION OF EMBODIMENTS OF THE INVENTION

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

Embodiments of the present invention can be broadly considered as having three stages: The first stage is the preparation of 2-carbomethoxytropinone (2-CMT) in the form of (+)-2-carbomethoxytropinone bitartrate; the second stage is the preparation of (−)-methylecgonine hydrochloride from the (+)-2-CMT; and the third stage is the preparation of (−)-cocaine from the (−)-methylecgonine hydrochloride. Each stage will be discussed in detail below and examples provided at the end of this specification.

Preparation of 2-Carbomethoxytropinone (2-CMT)

Figure 1:
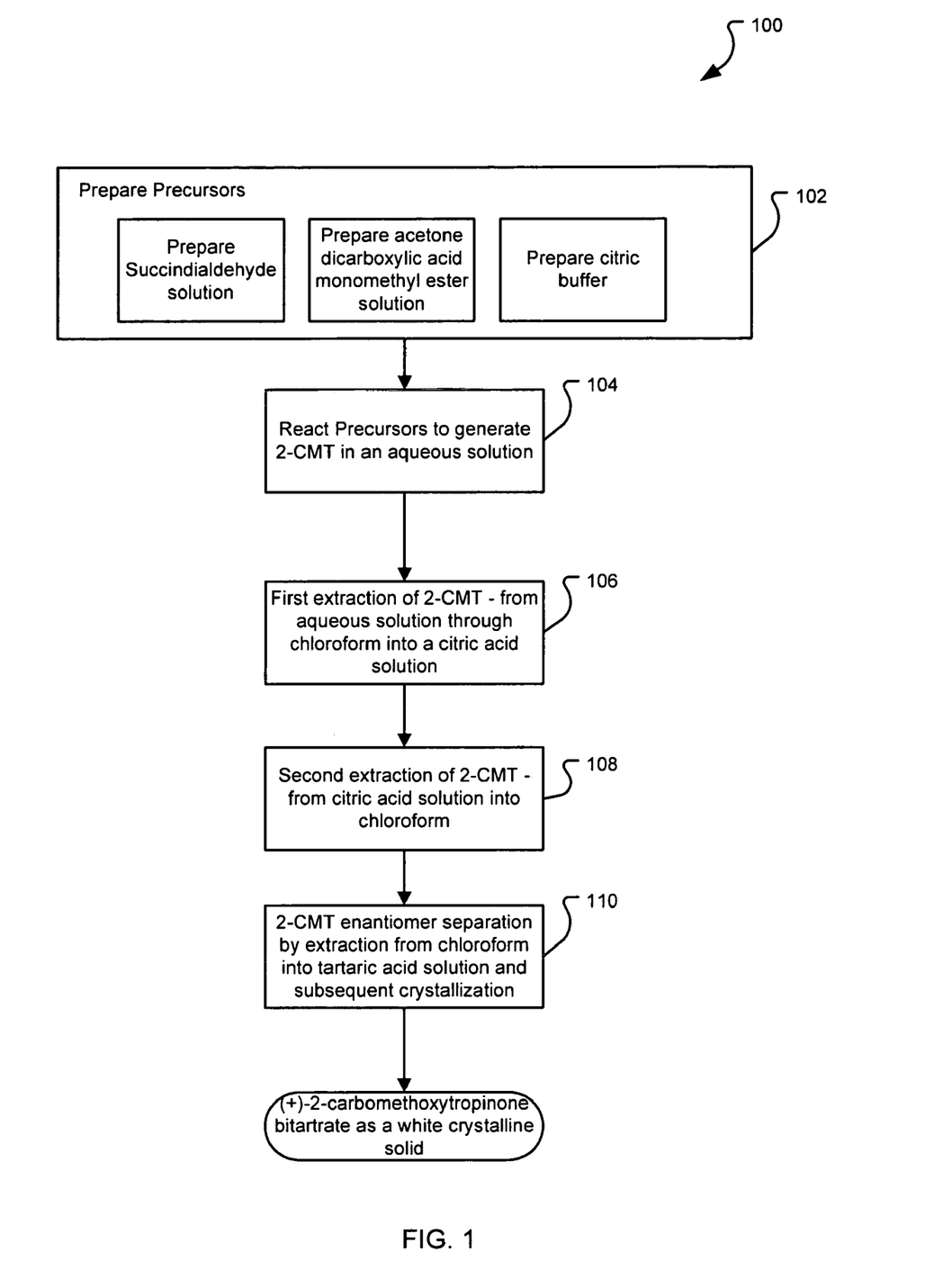
FIG. 1 is a flowchart showing the high-level operations involved in synthesizing (+)-2-CMT bitartrate in accordance with an embodiment of the present invention.

FIG. 1 is a flowchart showing the high-level operations involved in synthesizing 2-CMT in accordance with an embodiment of the present invention. In the embodiment shown, 2-CMT is synthesized from succindialdehyde, acetone dicarboxylic acid monomethyl ester and methylamine hydrochloride.

The first step of the synthesizing process 100 is to prepare the various precursor materials including the succindialdehyde and acetone dicarboxylic acid monomethyl ester in a prepare precursors operation 102. In one embodiment, the succindialdehyde is created by adding 2,5-dimethoxytetrahydrofurane to 0.2 N sulfuric acid with vigorous stirring. After the addition is complete, the mixture is slowly stirred at ambient temperature for 2.5-4 hours to give a solution of succindialdehyde. In this reaction, one mole of 2,5-dimethoxytetrahydrofurane gives one mole of succindialdehyde and the quantities used are dependent on the final amount of 2-CMT desired.

Separately, the acetone dicarboxylic acid monomethyl ester is created by adding acetonedicarboxylic acid anhydride to methanol cooled to 5-10° C. with vigorous stirring. The resulting solution is kept at ambient temperature for 0.5-1.5 hours to ensure that formation of acetone dicarboxylic acid monomethyl ester is complete. In this reaction, one mole of acetonedicarboxylic acid anhydride gives one mole of acetone dicarboxylic acid monomethyl ester and the quantities used are dependent on the final amount of 2-CMT desired.

A third solution for buffering is prepared. In an embodiment, a citrate buffer with a pH of about 4.5 is prepared with stirred citric acid and sodium hydroxide in water.

After the prepare precursors operation 102, a reaction operation 104 is performed in which the precursors are combined and allowed to react to form 2-CMT in an aqueous solution. In the reaction operation 104, the solution of citric acid and sodium hydroxide is cooled to 20-25° C. and then the acetonedicarboxylic acid monomethylester in methanol, succinedialdehyde in water described above and finally solid methylamine hydrochloride are added.

Figure 4:
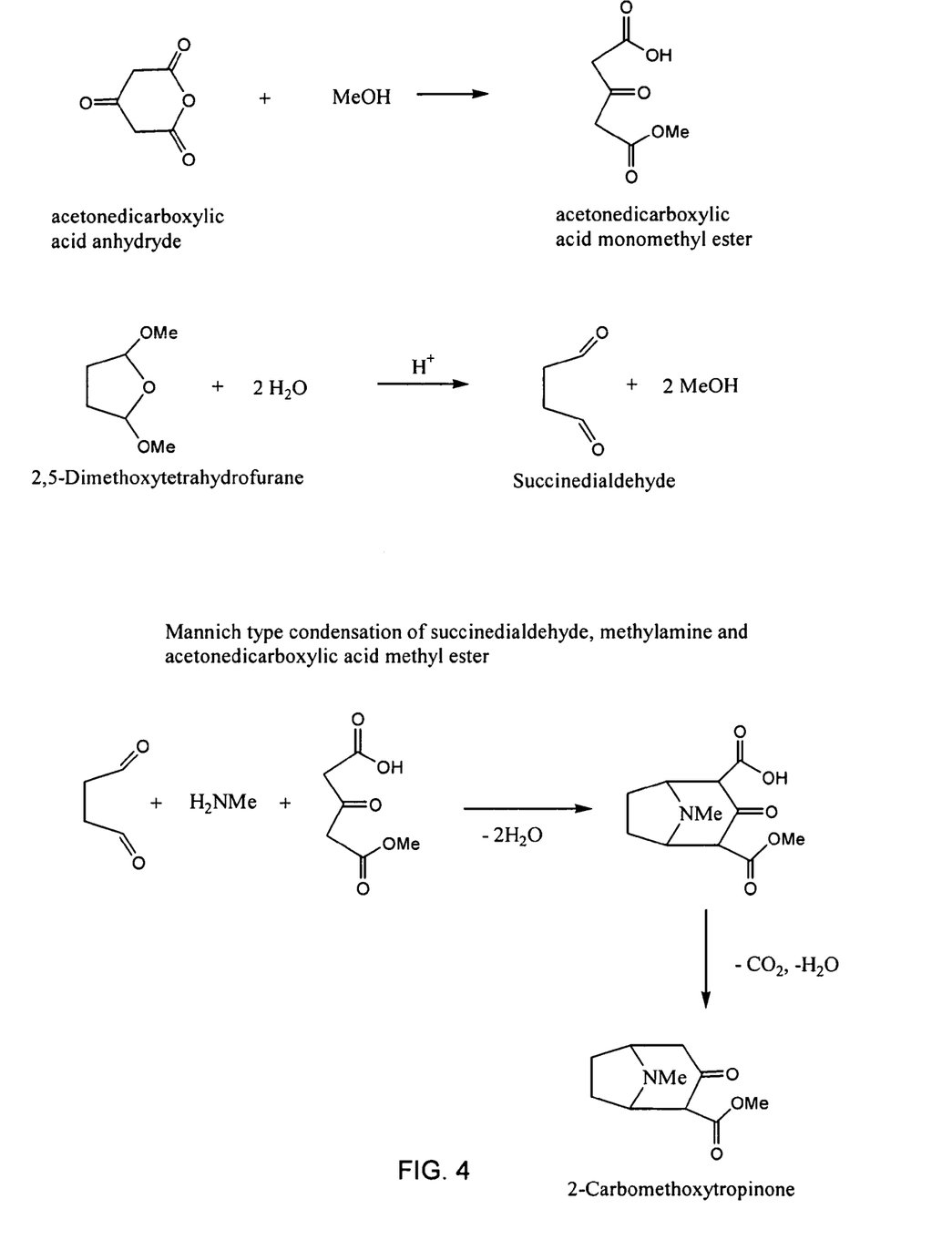
FIG. 4 is a representation of the reactions to form succindialdehyde, acetone dicarboxylic acid monomethyl ester and 2-CMT.

As the stoichiometry of the reaction to create 2-CMT requires a 1:1:1 molar ratio of succindialdehyde:acetone dicarboxylic acid monomethyl ester:methylamine hydrochloride and methylamine hydrochloride is the least expensive reagent in the reaction, in an embodiment an excess amount of methylamine hydrochloride is used relative to the succindialdehyde and acetone dicarboxylic acid monomethyl ester. In addition, succindialdehyde is prone to decomposition, as it may oxidize or undergo self-condensation, and, therefore, succindialdehyde may also be created in excess relative to the final amount of 2-CMT desired. A representation of the reactions to form succindialdehyde, acetone dicarboxylic acid monomethyl ester and 2-CMT is shown in FIG. 4.

The reaction mixture is slowly stirred at ambient temperature for 16-24 hours to ensure completion of the formation of 2-CMT. In an embodiment, a reaction time is chosen based on experience. In experiments performed (see examples below), a reaction time of 16-24 hours was selected based on previous experience. Alternatively, the reaction could be monitored until some predetermined 2-CMT conversion threshold is reached.

When sufficient reaction time has elapsed, the 2-CMT is extracted from the solution. In an embodiment, a first extraction operation 106 is performed to extract the 2-CMT from the solution. In an embodiment of the first extraction operation 106, the 2-CMT solution is treated with 50% NaOH upon vigorous stirring until pH 10-10.5. Any strong base such as NaOH, sodium carbonate or KOH can be used here to deprotonate 2-CMT and convert it into a salt insoluble in chloroform. However strong bases may cause saponification of the carbomethoxy group which is undesired. Lithium hydroxide is not strong enough to induce noticeable saponification, but is still able to deprotonate 2-CMT. For that reason, in an embodiment, lithium hydroxide monohydrate is added in a molar amount equal to 2-CMT to bring the pH up to a value to deprotonate the 2-CMT while limiting the amount of saponification. In another embodiment, lithium hydroxide may be used exclusively, which may even further reduce saponification, but will drastically increase the cost. In one embodiment, the pH was raised to between 11.5 and 12.5 and possibly further to approximately 13 to deprotonate the 2-CMT. After reaching the appropriate pH to deprotonate the 2-CMT, the mixture is stirred until all solids dissolve (about 10-20 min). The resulting solution is then washed with chloroform to remove impurities, such as side products, excess methylamine hydrochloride and some tropinione resulting from saponification of the carbomethoxy group.

Next, the washed 2-CMT solution is treated with an acid to convert deprotonated 2-CMT back to a chloroform soluble base. Hydrochloric, sulfuric or some other acid may be used to perform this. In an embodiment, solid ammonium chloride in an amount sufficient to raise the pH to between 9.5 and 10 is used.

After the pH has been adjusted with ammonium chloride, the chloroform extraction is performed. Chloroform is added to the solution containing the 2-CMT in a mixing vessel and the mixture is stirred. After sufficient stirring the chloroform layer is separated and subsequently extracted with a solution of an acid, such as for example citric acid, in water to yield an acidic solution containing 2-CMT. The chloroform is then recycled by returning it to the mixing vessel with the reaction mixture for second extraction. The amount of chloroform used depends on the amount of solution to be extracted and the number of extraction steps the practitioner is willing to perform to achieve the desired level of extraction of 2-CMT. The extraction—re-extraction process is repeated until the concentration of 2-CMT in the last extract is less than some target concentration, such as 1/10 of the concentration found in the first extract (analyzed by GC). The chloroform and the remaining reaction mixture can then be discarded. Alternatively, the chloroform may be reused, for example in the following second extraction operation 108 discussed below.

Next, a second extraction operation 108 is performed to remove the 2-CMT from the acidic solution. In the second extraction operation, the 2-CMT—acidic solution is cooled and basified, such as by treating the 2-CMT—acidic solution with ammonium hydroxide to bring the pH to between 8 and 9. The cooling is only necessary to prevent raising the temperature of the solution so high as to potentially affect the reaction. In an embodiment, the solution is cooled to between 0 to 20 C or further to between 5 and 10° C. The basified solution is then extracted again using a sufficient amount of chloroform. In one embodiment, four separate extractions are carried out and the chloroform (now containing 2-CMT) from each extraction is collected and mixed together to create a combined chloroform extract containing substantially racemic 2-CMT. The amount of the racemic 2-CMT in the combined chloroform extract can be determined by evaporating of an aliquot of the extract.

In an embodiment, an optional step of removing colored impurities from the substantially racemic 2-CMT obtained above is performed. An amount of silica gel is selected to achieve the color as desired. For example, in an embodiment the combined chloroform extract is then stirred with silica gel for 10-20 min and filtered. However, care should be taken as silica gel will absorb the desired product as well as the colored impurites, thus potentially reducing yield.

The embodiments described above discuss using chloroform for performing extractions from aqueous solutions. However, other organic solvents not miscible with water may be used for extractions in this specification such as chloroform, toluene, ethyl acetate, methylene chloride, carbon tetrachloride, and diethyl ether.

After the second extraction operation 108, the 2-CMT is converted to 2-CMT bitartrate in a 2-CMT enantiomer separation operation 110. In the enantiomer separation operation 110, the chloroform/(rac)-2-CMT solution is added to a solution of (+)-tartaric acid in water and the mixture is vigorously stirred for 5-10 min. An amount of tartaric acid sufficient to react with the 2-CMT is used. In an embodiment, 0.761 kg of (+)-tartaric acid/kg of 2-CMT was used and 1.98 L of water/kg of 2-CMT was used. This causes a separation to occur in which both enantiomers go to the aqueous phase to form diastereomeric salts with (+)-tartaric acid. One diastereomer ((+)-2-CMT-(+)-tartaric acid) is less soluble then another and partially precipitates from $H_2O$/MeOH mixture. The more soluble diastereomer ((−)-2-CMT-(+)-tartaric acid) remains in solution along with the rest of the less soluble diastereomer.

The aqueous phase is diluted with methanol and stirred slowly for 16-24 hours to crystallize the 2-CMT bitartarte. The amount of methanol used is a function of the amount of 2-CMT. Experiments have so far determined that a value of about 6.1 L of MeOH/kg of 2-CMT free base in the aqueous is optimal. More or less methanol can be used, but either the yield will be lower (as less of the desired diastereomer precipitates) or the purity may not be acceptable (as undesired diastereomer will precipitate along with the desired). An acceptable range for methanol in this operation is 1-10 L methanol/kg 2-CMT, a more acceptable range being 5-7 L methanol per kg of 2-CMT and an even more acceptable range being 5.5-6.5 L methanol per kg of 2-CMT. In an embodiment, other organic solvents miscible with water such as ethanol, isopropanol, acetone and so on can probably be used provided that the optimal ratio is found.

The amount of water used in the aqueous phase is also important. This is assumed to be due to the solubility of the product—if too much water is used there is no precipitation, and if too little water is used no separation occurs. In an embodiment, an acceptable range of water was 1-5 L of water/kg of 2-CMT, a more acceptable range was 1.5-2.5 L/kg, and an even more acceptable range was 1.9-2.1 L of water/kg of 2-CMT.

The formed crystals are separated by filtration and washed. In one embodiment, the crystals are washed twice with a minimum amount of methanol and washed twice again with acetone. Finally, the crystals are then dried at 75-80° C. to give (+)-2-carbomethoxytropinone bitartrate as a white crystalline solid. In experiments, the crystals are substantially pure in that purities greater than 90 and indeed greater than 99% and up to 100% of (+)-2-carbomethoxytropinone according to the value of optical rotation ($\alpha_D$) taken by standard methods, within the accuracy of the measurement, have been obtained.

In one embodiment of the 2-CMT enantiomer separation operation 110, the mother liquor is discarded even though it may contain a significant amount of both enantiomers of 2-CMT. While it is possible to recover the remaining (+)-2-CMT using conventional methods, such recovery is not currently cost effective in that while increasing the overall yield of (−)-2-CMT, it would also increase the overall cost per unit mass of 2-CMT.

Preparation of (−)-Methylecgonine Hydrochloride

Figure 5:
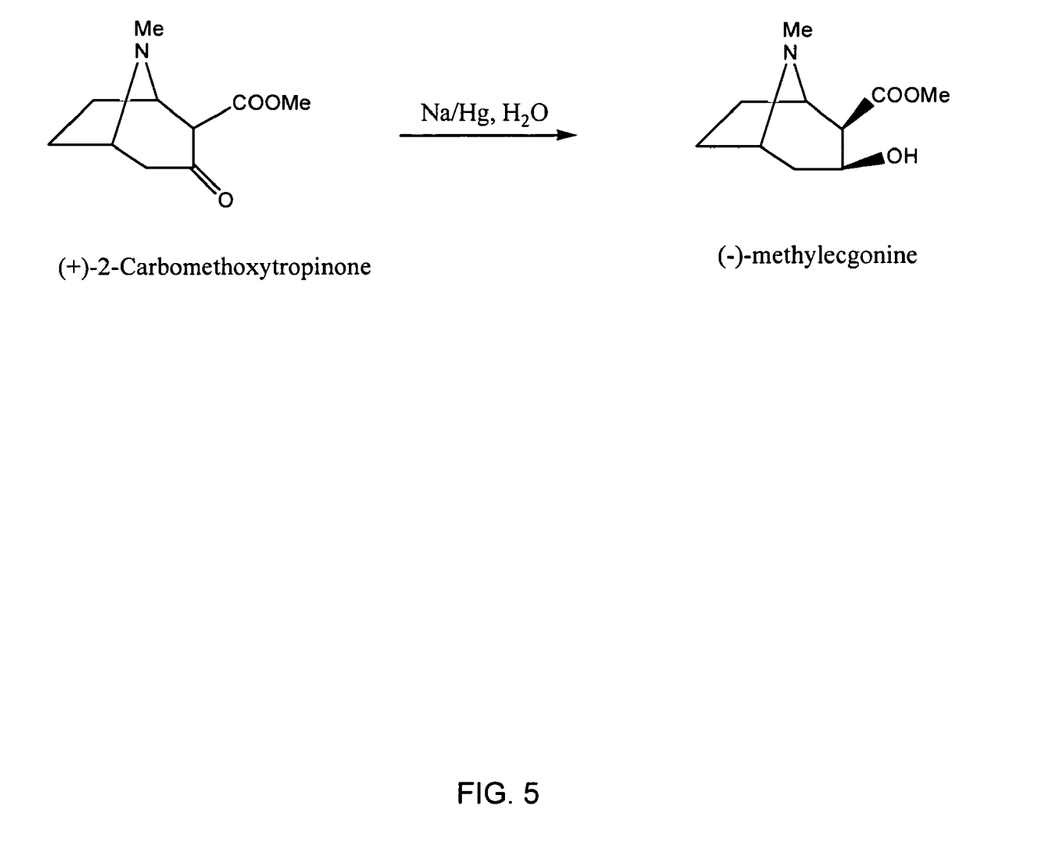
FIG. 5 illustrates the reaction of (+)-2-carbomethoxytropinone bitartrate into (−)-methylecgonine hydrochloride.

FIG. 5 illustrates the reaction of (+)-2-carbomethoxytropinone bitartrate into (−)-methylecgonine hydrochloride. The following prophetic example illustrates a system and method of preparing (−)-methylecgonine hydrochloride in a large scale using a continuous electrolysis process for creating and supplying sodium amalgam. In the prophetic example, the preparation of (−)-methylecgonine hydrochloride utilizes a reactor connected via the bottom drain to an electrolyzing unit. In an embodiment, the reactor is a fiberglass reactor equipped with a cooling coil and an efficient mechanical stirrer. In addition, a mechanism is provided that transfers amalgam generated in the electrolyzing unit to the reactor. Such a transfer mechanism may be automated to continuously transfer the amalgam to the reactor.

Figure 2:
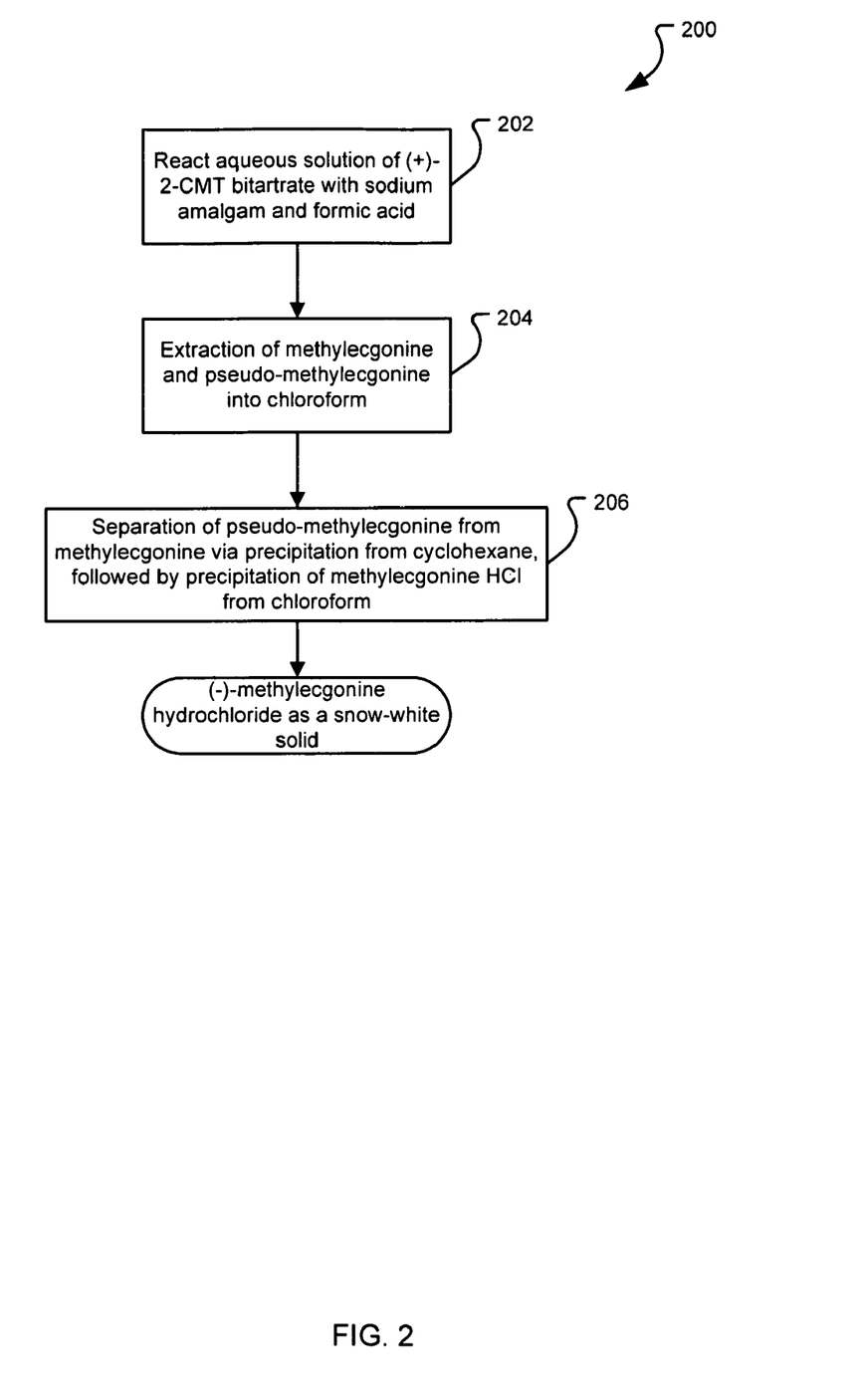
FIG. 2 is a flowchart showing the high-level operations involved in synthesizing (−)-methylecgonine hydrochloride in accordance with an embodiment of the present invention.

FIG. 2 is a flowchart showing the high-level operations involved in synthesizing (−)-methylecgonine hydrochloride in accordance with an embodiment of the present invention.

The synthesizing (−)-methylecgonine hydrochloride process 200 begins with an electrolysis operation 202. In electrolysis operation 202, direct electric current is passed through 40% NaOH with a mercury cathode and Ni anode in the electrolyzing unit. Other anode materials are possible but they are either expensive such as palladium and platinum, or will corrode extensively such as graphite. The reactor, connected to the electrolyzing unit is charged with water and (+)-2-carbomethoxytropinone bitartrate. For the crystals to completely dissolve in the water, the pH should be maintained above 4.0, and further above 4.5. The (+)-2-carbomethoxytropinone bitartrate may have been generated as described with reference to FIG. 1, above, or obtained through some other method.

After the crystals have been dissolved, the pH of the stirred mixture in the reactor is then adjusted to an optimal range to balance both speed of reaction and yield, such as between pH of 4 to 7, further between 5 and 6, and still further at about pH 5.5. The pH is adjusted by addition of 40% sodium hydroxide and the resulting solution is cooled to 2-5° C.

As direct electric current is passed through the electrolyzing unit, formation of sodium amalgam occurs that is pumped to the reactor from the electrolyzing unit. In one embodiment, the formed amalgam is constantly pumped to the top inlet of the reactor. The temperature of the reaction mixture is kept at 0-5° C. using the reactor's cooling element.

During the reaction, the pH of the solution is maintained at 5.4-5.9 by addition of an acid that forms a highly soluble sodium salt, such as formic acid. Although any acid can be used, acids with highly soluble sodium salts have been found to have special properties for this application. For the purposes of this specification, an acid that forms a highly soluble sodium salt is an acid that forms a sodium salt that is at least 1.5 times more soluble than sodium sulfate in water at a pH of 5.6 and at a temperature of 5° C. Sulfuric acid is not preferred as it forms sodium sulfate which is only moderately soluble in water. Therefore more water is necessary to keep all salts in solution. Sodium formate is approximately 4 times more soluble than the sulfate. Therefore, the reaction solution can be 4 times more concentrated, which reduces the size of the equipment as well as the cost of running the electrolysis. There are other acids, which form highly soluble sodium salts such as acetic, propionic, phosphoric or more expensive trifluoroacetic, choroacetic and perhaps many more.

During the electrolysis operation 202 sodium amalgam is constantly made by electrolysis and pumped to the reactor where it reacts with 2-carbomethoxytropinone. Spent amalgam depleted of sodium flows back to the electrolyzing unit where it is replenished with sodium. The process continues until substantially all 2-carbomethoxytropinone is converted. Thus two separate steps: preparation of sodium amalgam and reduction of 2-carbomethoxytropinone are combined into a single uninterrupted process.

The reaction cause's the conversion of 2-carbomethoxytropinone into methylecgonine and pseudo-methylecgonine. In an embodiment, the process is continued until the conversion of 2-carbomethoxytropinone into methylecgonine and pseudo-methylecgonine exceeds 95% (as determined by gas chromatography). The time required to achieve this conversion will vary depending on the exact equipment used as well as such variables as the current supplied in the electrolysis unit, the amount of mercury used, and the pH. Alternatively, the electrolysis could be performed for a predetermined period of time or until some predetermined conversion threshold is reached.

After the reaction, the aqueous solution is removed from the reactor and possible traces of mercury are separated. In one embodiment, carbon is added to the aqueous solution and the mixture is stirred and then filtered to remove the carbon which absorbs any traces of mercury. Other methods of removing possible mercury contaminations from the aqueous solution are also possible.

Next, an extraction operation 204 is performed to extract the methylecgonine and pseudo-methylecgonine from the filtered solution using methods known in the art to give pale yellow oil, which contains a mixture of methylecgonine and pseudo-methylecgonine.

Next, the pseudo-methylecgonine is separated from the methylecgonine in a separation operation 206. In an embodiment, the separation may be conducted using two steps. In the first step of the separation operation 206, the oil is dissolved in a sufficient amount of cyclohexane. The pseudo-methylecgonine will partially precipitate out of the cyclohexane solution over time. In one embodiment, the cyclohexane solution is allowed to stand for 4-16 hours to allow sufficient time for the precipitation to occur. The precipitated pseudo-methylecgonine is separated from the cyclohexane mixture by filtration.

The filtrate is then evaporated to give pale yellow oil (which is a mixture of (−)-methylecgonine and (+)-pseudo-methylecgonine but which is substantially enriched with methylecgonine). Prior to evaporation, the filtrate may be stirred with silica gel, and filtered again to remove any impurities.

In the second part of the separation operation 206, the remaining pseudo-methylecgonine may be removed by methods known in the art. For example, separation is achieved by converting the methylecgonine and pseudo-methylecgonine to the corresponding hydrochlorides. Methylecgonine hydrochloride is practically insoluble in chloroform and precipitates, while pseudo-methylecgonine-HCl remains in solution. The precipitate may be removed by filtration and washed or otherwise purified to improve the purity of the methylecgonine hydrochloride. For example, in one embodiment, after filtering the formed solid is washed with chloroform twice and re-dissolved in a sufficient quantity of methanol, which is then evaporated to dryness. The solid residue is then stirred with a sufficient amount of chloroform, filtered again, washed with twice chloroform, washed twice again with hexane or some other volatile solvent to remove the chloroform and dried on air to give (−)-methylecgonine hydrochloride as a snow-white solid.

Figure 3:
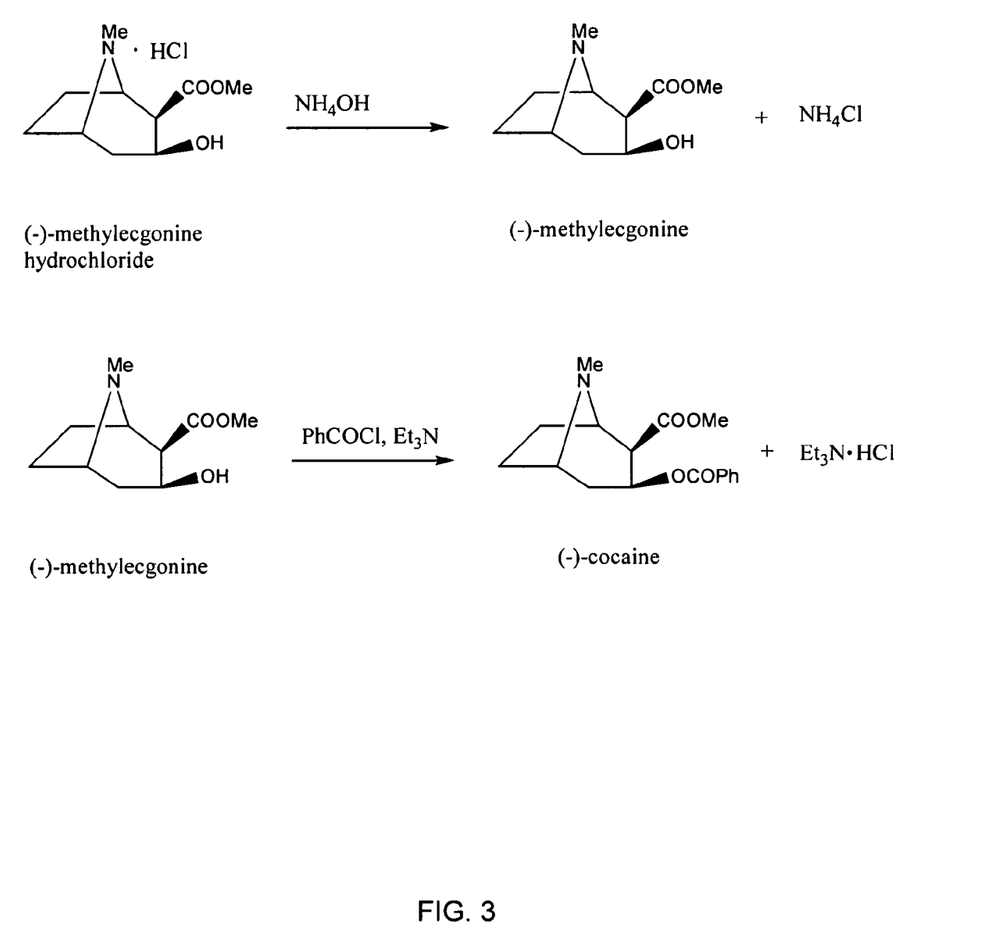
FIG. 3 illustrates the conversion of (−)-methylecgonine hydrochloride into (−)-cocaine.

(−)-cocaine can now be produced from the (−)-methylecgonine hydrochloride by methods known in the art. FIG. 3 illustrates the reaction of (−)-methylecgonine hydrochloride into (−)-cocaine. The (−)-cocaine created by this process can then be used as a component in the manufacture of other products.

EXAMPLES

Using the methodology described above with reference to FIG. 1, (+)-2-carbomethoxytropinone bitartrate was synthesized. In the synthesis, 33.87 kg of 2,5-dimethoxytetrahydrofurane was added to 0.2 N sulfuric acid (150 L) upon vigorous stirring. The mixture was slowly stirred at ambient temperature for 2.5 hours to give a solution of succindialdehyde.

Acetonedicarboxylic acid anhydride (31.4 kg) was added to methanol (100 L) cooled to 5° C. upon vigorous stirring. The resulting solution was kept at ambient temperature for 45 min to ensure that formation of acetone dicarboxylic acid monomethyl ester was complete.

A stirred solution of citric acid (60.0 kg) and sodium hydroxide (26.7 kg) in water (225 L) was prepared and cooled to 20° C. The solution was combined with the succindialdehyde solution then with the acetonedicarboxylic acid monomethylester in methanol (see above) and finally with methylamine hydrochloride (25.0 kg). The reaction mixture was slowly stirred at ambient temperature for 16 hours. After which time, the mixture was treated with an aqueous solution of 50% NaOH upon vigorous stirring until pH 11.0.

Lithium hydroxide monohydrate (10.7 kg) was added and the mixture was stirred until all solids dissolved, which took 10 minutes. The resulting solution was washed with chloroform twice using 75 liters of chloroform each time. Ammonium chloride was then added to the solution as a solid until the pH was 9.5. Then 150 L of chloroform was added and the resulting mixture was stirred for 10-15 minutes.

The chloroform layer was drained from the vessel containing the mixture and extracted with a solution of citric acid (57 kg) in water (135 L) to yield a solution containing 2-CMT citrate. The chloroform was then separated and returned to the vessel with the reaction mixture for second extraction. The extraction—re-extraction process was repeated 5 times at which time the concentration of 2-CMT in the last extract was about $\frac{1}{10}$ of the concentration found in the first extract (analyzed by GC). Subsequently, the chloroform and the reaction mixture were discarded.

The 2-CMT—citric acid solution was cooled to 5° C. and treated with ammonium hydroxide upon vigorous stirring until the pH was about 9. The solution was then extracted four times with 60 L chloroform. The chloroform extracts were combined, stirred with silica gel (8 kg) for about 20 minutes and filtered. The amount of the 2-CMT obtained was determined by evaporating of an aliquot of the filtrate. In the experiment, the yield of (rac)-2-CMT thus determined was 37.7 kg or about 78% of that theoretically possible from 31.4 kg of acetonedicarboxylic acid anhydride. The chloroform filtrate was added to a solution of (+)-tartaric acid (28.69 kg) in water (62.2 L) and the mixture was vigorously stirred for about 5 min. The chloroform phase was separated and discarded. The aqueous phase was diluted with methanol (191.5 L) and stirred slowly for about 20 hours. The formed crystals were separated by filtration then washed twice with a minimum amount of methanol. Subsequently, the crystals were again washed twice with acetone (20 L each time). Finally, the crystals were dried at 85-90° C. to give 17.92 kg (54%) of (+)-2-carbomethoxytropinone bitartrate as a white crystalline solid. $[\alpha]_D^{24}$+17° (c=2, H$_2$O).

Using the methodology described above with reference to FIG. 2, (−)-methylecgonine hydrochloride was synthesized from the (+)-2-carbomethoxytropinone bitartrate created above. A 250 mL jacketed reactor, equipped with mechanical stirrer and connected via the bottom drain to an electrolyzing unit, which contained mercury (1000 g) and 40% NaOH (150 mL), was charged with water (80 mL) and (+)-2-carbomethoxytropinone bitartrate (18.2 g). The pH of the stirred mixture was adjusted to 5.5 by addition of 40% sodium hydroxide and the resulting solution was cooled to 5° C. Direct electric current (4.5 A, 7-12 V) was passed through the electrolyzing unit with nickel anode and mercury cathode. The formed amalgam was pumped by a peristaltic pump to the top inlet of the jacketed reactor and allowed to flow back through the bottom drain to the electrolyzing unit. The temperature of the reaction mixture was kept at 0-5° C. and pH was constantly monitored and adjusted to 5.4-5.9 by addition of formic acid. After 4 hours conversion of 2-carbomethoxytropinone was 95% (determined by GC). The aqueous solution was siphoned from the reactor, stirred with carbon (2 g) and filtered to remove possible traces of mercury. The filtrate was brought to pH 9.5 by addition of ammonium hydroxide and extracted with chloroform (4×80 mL). Combined extracts were dried over sodium carbonate and evaporated to give pale yellow oil (9.4 g, 3:2 mixture of methylecgonine and pseudo-methylecgonine by GC). The oil was dissolved in cyclohexane (80 mL) and set aside for 4 hours. The precipitated pseudo-methylecgonine was separated by filtration, the filtrate was stirred with silica gel (3 g), filtered and evaporated to give pale yellow oil (6.3 g, 4:1 mixture of methylecgonine and pseudo-methylecgonine by GC). The oil was dissolved in chloroform (30 mL) and treated with 4.2 M solution of hydrogen chloride in ether (8 mL) upon vigorous stirring. The formed solid was filtered, washed with chloroform (2×15 mL) and re-dissolved in methanol (30 mL). The resulting solution was evaporated to dryness. The solid residue was stirred with chloroform (20 mL), filtered, washed with chloroform (2×15 mL), hexane (2×15 mL) and dried on air to give methylecgonine hydrochloride as a snow-white solid. The yield was 3.94 g, 32%.

Using the methodology described above with reference to FIG. 3, (−)-cocaine was synthesized from the (−)-methylecgonine hydrochloride created above. A stirred solution of methylecgonine hydrochloride (3.74 kg) in water (10 L) was treated with chloroform (30 L) and ammonium hydroxide (2 L). The bottom (chloroform) layer was separated and the aqueous phase was extracted with additional chloroform (10 L). The separated chloroform layer and the chloroform extract were combined and the combined chloroform extract was dried over sodium carbonate, filtered and treated with triethylamine (4.8 kg) and benzoyl chloride (4.46 kg).

The resulting solution was stirred at ambient temperature for about 24 hours, and cooled to 10° C. The cooled solution was then mixed with 1.5 N hydrochloric acid (45 L) and stirred for 30 min. The upper layer was separated and the organic phase was extracted with water (10 L). The removed upper aqueous layer was combined with the aqueous extract to form a combined aqueous solution. The combined aqueous solution was washed with chloroform (10 L). Then ammonium hydroxide was added until the pH of the combined aqueous solution was 9. After the pH adjustment, the combined aqueous solution was extracted with chloroform twice using 20 L of chloroform each time. The combined chloroform extract was dried over sodium carbonate, filtered and evaporated to give yellow oil. The oil was dissolved in tert-butyl methyl ether (30 L), stirred with silica gel (300 g) and filtered. The filtrate was diluted with heptane (50 L), concentrated to ca 50 L by distillation, cooled to 5-10° C. and slowly stirred for 2-4 hours. The formed crystals were filtered, washed with cold hexane and dried on air to give (−)-cocaine as a snow—white crystalline solid. A second crop was isolated upon concentration of the mother liquor. The total yield was 3.85 kg, or 80% of the theoretical limit when starting with 3.74 kg of (−)-methylecgonine hydrochloride.

While the invention has been described in detail and with reference to specific embodiments thereof, it will be apparent to those skilled in the art that various changes and modifications can be made therein without departing from the spirit and scope thereof. Thus, it is intended that the present invention cover the modifications and variations of this invention provided they come within the scope of the appended claims and their equivalents.

What is claimed is:
1. A method of manufacturing (−)cocaine comprising:
reacting an aqueous solution of (+)-2-carbomethoxytropinone bitartrate, sodium amalgam and an acid that forms a highly soluble sodium salt whereby at least some of the (+)-2-carbomethoxytropinone bitartrate is converted to (−)-methylecgonine;
converting the (−)-methylecgonine into (−)-cocaine.

2. The method of claim 1 wherein reacting further comprises:
continuously supplying sodium amalgam from an electrolyzing unit to a reactor containing the aqueous solution of (+)-2-carbomethoxytropinone bitartrate and the acid that forms a highly soluble sodium salt; and
continuously transferring spent amalgam from the reactor to the electrolyzing unit.

3. The method of claim 1 further comprising:
preparing the aqueous solution of (+)-2-carbomethoxytropinone bitartrate by
adding (rac)-2-CMT in organic solvent not miscible with water to a solution of (+)-tartaric acid in water to create an aqueous phase having diastereomeric salts of 2-CMT with (+)-tartaric acid;
adding an organic solvent miscible with water to the aqueous phase;
drying crystals obtained from the combined aqueous phase and organic solvent to obtain substantially pure crystalline (+)-2-carbomethoxytropinone bitartrate; and
dissolving the substantially pure crystalline (+)-2-carbomethoxytropinone bitartrate in water.

4. The method of claim 3 further comprising:
preparing the (rac)-2-CMT by
extracting 2-CMT from an aqueous reaction mixture with a solvent to obtain an extract; and
extracting the extract with an acidic aqueous solution to form a soluble salt of 2-CMT in the acidic aqueous solution.

5. The method of claim 4 wherein preparing the (rac)-2-CMT further comprises:
repeating the two extracting operations of claim 4 until a predetermined amount of 2-CMT is transferred from the aqueous reaction mixture to the acidic aqueous solution.

6. The method of claim 5 wherein preparing the (rac)-2-CMT further comprises:
basifying the acidic aqueous solution; and
extracting (rac)-2-CMT from the basified acidic aqueous solution with a solvent.

7. The method of claim 4 wherein the acidic aqueous solution is an aqueous solution of an acid, wherein the acid is selected from citric acid, acetic acid, formic acid, tartaric acid and hydrochloric acid.

8. The method of claim 3 wherein the organic solvent miscible with water is selected from methanol, ethanol, isopropanol, and acetone.

9. The method of claim 1 wherein the acid that forms a highly soluble sodium salt is one or more acids selected from formic acid, acetic acid, propionic acid, phosphoric acid, trifluoroacetic acid, and choroacetic acid.

10. The method of claim 1 wherein the acid that forms a highly soluble sodium salt is an acid that forms a sodium salt that is at least 1.5 times more soluble than sodium sulfate in water at a pH of 5.6 and at a temperature of 5° C.

11. A method for preparing (+)-2-carbomethoxytropinone bitartrate comprising:
adding (rac)-2-carbomethoxytropinone in a first organic solvent not miscible with water to a solution of (+)-tartaric acid in water to create an aqueous phase having diastereomeric salts of 2-carbomethoxytropinone with (+)-tartaric acid;
adding a second organic solvent miscible with water to the aqueous phase to create crystalline (+)-2-carbomethoxytropinone bitartrate.

12. The method of claim 11 further comprising:
preparing the (rac)-2-carbomethoxytropinone by
extracting 2-carbomethoxytropinone (2-CMT) from an aqueous reaction mixture with a third organic solvent not miscible with water to obtain an extract; and
extracting the extract with an acidic aqueous solution to form a soluble salt of 2-CMT.

13. The method of claim 12 wherein preparing the (rac)-2-CMT further comprises:
repeating the two extracting operations of claim 12 until a predetermined amount of 2-CMT is transferred from the aqueous reaction mixture to the acidic aqueous solution.

14. The method of claim 13 wherein preparing the (rac)-2-CMT further comprises:
basifying the acidic aqueous solution; and
extracting (rac)-2-CMT from the basified acidic aqueous solution with the first organic solvent not miscible with water to obtain the (rac)-2-carbomethoxytropinone in a first organic solvent not miscible with water.

15. The method of claim 12 wherein the acidic aqueous solution is an aqueous solution of an acid, wherein the acid is selected from citric acid, acetic acid, formic acid, tartaric acid and hydrochloric acid.

16. The method of claim 11 wherein the second organic solvent miscible with water is selected from methanol, ethanol, isopropanol, and acetone.

17. The method of claim 15 wherein the first and third organic solvents not miscible with water are independently selected from chloroform, ethyl acetate, toluene, methylene chloride, carbon tetrachloride, and diethyl ether.

18. The method of claim 11 wherein the second organic solvent is methanol in an amount of 5.5 to 6.5 liters of methanol per kilogram of 2-carbomethoxytropinone.

19. The method of claim 11 wherein the crystalline (+)-2-carbomethoxytropinone bitartrate is substantially pure.

20. A method of creating methylecgonine and pseudomethylecgonine comprising:
reacting an aqueous solution of (+)-2-carbomethoxytropinone bitartrate, sodium amalgam and an acid that forms a highly soluble sodium salt whereby at least some of the (+)-2-carbomethoxytropinone bitartrate is converted to (−)-methylecgonine and (+)-pseudomethylecgonine.

21. The method of claim 20 wherein reacting further comprises:
continuously supplying sodium amalgam from an electrolyzing unit to a reactor containing the aqueous solution of (+)-2-carbomethoxytropinone bitartrate and an acid that forms a highly soluble sodium salt; and
continuously transferring spent amalgam from the reactor to the electrolyzing unit.

22. The method of claim 20 wherein the acid that forms a highly soluble sodium salt is one or more acids selected from formic acid, acetic acid, propionic acid, phosphoric acid, trifluoroacetic acid, and choroacetic acid.

23. The method of claim 20 wherein the acid that forms a highly soluble sodium salt is an acid that forms a sodium salt that is at least 1.5 times more soluble than sodium sulfate in water at a pH of 5.6 and at a temperature of 5° C.

24. A method of manufacturing (−)cocaine comprising:
reacting an aqueous solution of (+)-2-carbomethoxytropinone bitartrate, sodium amalgam and an acid to form (−)-methylecgonine; and
converting the (−)-methylecgonine into (−)-cocaine.

* * * * *